United States Patent
Spratt et al.

(10) Patent No.: US 9,724,145 B2
(45) Date of Patent: Aug. 8, 2017

(54) BONE ANCHOR ASSEMBLIES WITH MULTIPLE COMPONENT BOTTOM LOADING BONE ANCHORS

(71) Applicant: Medos International Sarl, Le Locle (CH)

(72) Inventors: Frank Spratt, Bole (CH); Thibault Chandanson, Villers le Lac (FR)

(73) Assignee: Medos International Sarl, Le Locle (CH)

( * ) Notice: Subject to any disclaimer, the term of this patent is extended or adjusted under 35 U.S.C. 154(b) by 286 days.

(21) Appl. No.: 13/828,236

(22) Filed: Mar. 14, 2013

(65) Prior Publication Data

US 2014/0277189 A1 Sep. 18, 2014

(51) Int. Cl.
*A61B 17/70* (2006.01)
*A61B 17/86* (2006.01)

(52) U.S. Cl.
CPC ...... *A61B 17/8605* (2013.01); *A61B 17/7038* (2013.01); *A61B 17/863* (2013.01); *Y10T 29/49826* (2015.01)

(58) Field of Classification Search
CPC ............ A61B 17/7032; A61B 17/7034; A61B 17/7035; A61B 17/7037
USPC .................. 606/264–278, 300–321
See application file for complete search history.

(56) References Cited

U.S. PATENT DOCUMENTS

| | | | |
|---|---|---|---|
| 2,788,045 A | 4/1957 | Rosan | |
| 2,842,180 A | 7/1958 | Brown et al. | |
| 4,124,318 A | 11/1978 | Sagady | |
| 4,762,024 A | 8/1988 | Graft | |

(Continued)

FOREIGN PATENT DOCUMENTS

| | | |
|---|---|---|
| DE | 29903342 U1 | 6/1999 |
| EP | 0 470 660 B1 | 7/1995 |

(Continued)

OTHER PUBLICATIONS

[No Author Listed] Definition of "clip," www.thefreedictionary.com/clip; accessed May 16, 2015.

(Continued)

*Primary Examiner* — Ellen C Hammond
*Assistant Examiner* — Christina Negrellirodrigue
(74) *Attorney, Agent, or Firm* — Nutter McClennen & Fish LLP

(57) ABSTRACT

Bone anchor assemblies and methods are provided having a multi-component bone anchor that is configured to allow the shank of the bone anchor to be bottom loaded into a receiver member. In one embodiment, a bone anchor assembly is provided having a shank with a distal threaded portion and a proximal head portion, a receiver member having an aperture formed in a distal end thereof through which the head portion of the shank can be received, the receiver member defining a polyaxial seat, a non-expandable outer ring configured to be polyaxially disposed within the polyaxial seat of the receiver member and defining a central opening through which the head portion of the shank can be received, and an expandable inner ring having an inner surface configured to mate with the head portion of the shank and an outer surface configured to mate with an inner surface of the outer ring to thereby lock the outer ring in a fixed position relative to the shank.

21 Claims, 16 Drawing Sheets

(56) References Cited

U.S. PATENT DOCUMENTS

| | | |
|---|---|---|
| 5,009,017 A | 4/1991 | Diekevers et al. |
| 5,129,388 A | 7/1992 | Vignaud et al. |
| 5,154,719 A | 10/1992 | Cotrel |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried et al. |
| 5,643,260 A | 7/1997 | Doherty |
| 5,672,176 A | 9/1997 | Biedermann et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B2 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,942 B2 | 5/2010 | Schumacher |
| 7,722,649 B2 | 5/2010 | Biedermann et al. |
| 7,727,261 B2 | 6/2010 | Barker et al. |
| 7,731,736 B2 | 6/2010 | Guenther et al. |
| 7,736,380 B2 | 6/2010 | Johnston et al. |
| 7,766,946 B2 | 8/2010 | Bailly |
| 7,785,354 B2 | 8/2010 | Biedermann et al. |
| 7,789,900 B2 | 9/2010 | Levy et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,173 B2 | 5/2011 | Hammill, Sr. et al. |
| 7,951,175 B2 | 5/2011 | Chao et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,052,724 B2 | 11/2011 | Jackson |
| 8,057,518 B2 | 11/2011 | Frasier et al. |
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,308,782 B2 | 11/2012 | Jackson |
| 8,313,515 B2 | 11/2012 | Brennan et al. |
| 8,313,516 B2 | 11/2012 | Konieczynski et al. |

(56) References Cited

U.S. PATENT DOCUMENTS

| | | |
|---|---|---|
| 8,337,530 B2 | 12/2012 | Hestad et al. |
| 8,343,191 B2 | 1/2013 | Matthis et al. |
| 8,377,100 B2 | 2/2013 | Jackson |
| 8,409,260 B2 | 4/2013 | Biedermann et al. |
| 8,430,914 B2 | 4/2013 | Spratt et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,608,746 B2 | 12/2013 | Kolb et al. |
| 8,951,294 B2 | 2/2015 | Gennari et al. |
| 9,155,580 B2 | 10/2015 | Cormier et al. |
| 9,259,247 B2 | 2/2016 | Chandanson et al. |
| 2002/0133159 A1 | 9/2002 | Jackson |
| 2003/0023243 A1 | 1/2003 | Biedermann et al. |
| 2003/0055426 A1 | 3/2003 | Carbone et al. |
| 2003/0073996 A1 | 4/2003 | Doubler et al. |
| 2003/0100896 A1 | 5/2003 | Biedermann et al. |
| 2003/0125741 A1 | 7/2003 | Biedermann et al. |
| 2003/0153911 A1 | 8/2003 | Shluzas |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1* | 9/2005 | Biedermann ...... A61B 17/7032 606/279 |
| 2005/0228326 A1 | 10/2005 | Kalfas et al. |
| 2005/0273101 A1 | 12/2005 | Schumacher |
| 2005/0277928 A1 | 12/2005 | Boschert |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0149241 A1 | 7/2006 | Richelsoph et al. |
| 2006/0161153 A1 | 7/2006 | Hawkes et al. |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055244 A1 | 3/2007 | Jackson |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon et al. |
| 2007/0260246 A1 | 11/2007 | Biedermann |
| 2007/0265621 A1 | 11/2007 | Matthis et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1* | 7/2008 | Nilsson ............ A61B 17/7032 606/266 |
| 2008/0200956 A1 | 8/2008 | Beckwith et al. |
| 2008/0215100 A1* | 9/2008 | Matthis ............ A61B 17/7032 606/309 |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1* | 11/2008 | Peterson ............ A61B 17/7032 606/305 |
| 2008/0312692 A1 | 12/2008 | Brennan et al. |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 | 8/2009 | Hutchinson |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264933 A1 | 10/2009 | Carls et al. |
| 2009/0287261 A1 | 11/2009 | Jackson |
| 2009/0326587 A1 | 12/2009 | Matthis et al. |
| 2010/0004693 A1 | 1/2010 | Miller et al. |
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0305621 A1 | 12/2010 | Wang et al. |
| 2010/0312279 A1 | 12/2010 | Gephart et al. |
| 2011/0046683 A1 | 2/2011 | Biedermann et al. |
| 2011/0106179 A1 | 5/2011 | Prevost et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1* | 2/2012 | Jackson ............ A61B 17/7032 606/305 |
| 2012/0046701 A1* | 2/2012 | Gennari ............ A61B 17/7076 606/308 |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1 | 5/2012 | Biedermann et al. |
| 2012/0143266 A1 | 6/2012 | Jackson et al. |
| 2012/0150239 A1 | 6/2012 | Garamszegi |
| 2012/0165882 A1 | 6/2012 | Biedermann et al. |
| 2012/0179209 A1 | 7/2012 | Biedermann et al. |
| 2012/0185003 A1 | 7/2012 | Biedermann et al. |
| 2012/0197313 A1 | 8/2012 | Cowan |
| 2012/0209336 A1 | 8/2012 | Jackson et al. |
| 2012/0253404 A1 | 10/2012 | Timm et al. |
| 2012/0277805 A1 | 11/2012 | Farris |
| 2012/0303070 A1 | 11/2012 | Jackson |
| 2012/0310290 A1 | 12/2012 | Jackson |
| 2012/0316605 A1 | 12/2012 | Palagi |
| 2012/0328394 A1 | 12/2012 | Biedermann et al. |
| 2012/0330364 A1 | 12/2012 | Jacofsky et al. |
| 2013/0013003 A1 | 1/2013 | Carbone et al. |
| 2013/0053901 A1 | 2/2013 | Cormier et al. |
| 2013/0096618 A1 | 4/2013 | Chandanson et al. |

(56) References Cited

U.S. PATENT DOCUMENTS

| | | |
|---|---|---|
| 2013/0096623 A1 | 4/2013 | Biedermann et al. |
| 2013/0103093 A1 | 4/2013 | Biedermann et al. |
| 2013/0110172 A1 | 5/2013 | Biedermann et al. |
| 2013/0110180 A1 | 5/2013 | Doubler et al. |
| 2013/0211467 A1 | 8/2013 | Dickinson |
| 2014/0018861 A1 | 1/2014 | Hutchinson |
| 2014/0025119 A1 | 1/2014 | Biedermann et al. |
| 2014/0094849 A1 | 4/2014 | Spratt et al. |
| 2014/0142633 A1 | 5/2014 | Jackson et al. |
| 2014/0277153 A1 | 9/2014 | Spratt et al. |
| 2014/0277157 A1 | 9/2014 | Chandanson et al. |
| 2014/0277158 A1 | 9/2014 | Spratt et al. |
| 2014/0277161 A1 | 9/2014 | Spratt et al. |
| 2014/0277162 A1 | 9/2014 | Kostuik et al. |
| 2016/0128733 A1 | 5/2016 | Spratt et al. |
| 2016/0135848 A1 | 5/2016 | Chandanson et al. |

FOREIGN PATENT DOCUMENTS

| | | |
|---|---|---|
| EP | 1 295 566 A1 | 3/2003 |
| EP | 0 857 465 B1 | 6/2003 |
| EP | 1 570 794 A1 | 9/2005 |
| EP | 1 774 919 B1 | 8/2008 |
| EP | 1 795 134 B1 | 8/2008 |
| EP | 2 070 485 A1 | 6/2009 |
| EP | 1 694 229 B1 | 7/2010 |
| EP | 2 272 451 A1 | 1/2011 |
| EP | 2 286 748 A1 | 2/2011 |
| EP | 2 455 028 A1 | 5/2012 |
| EP | 2 129 310 B1 | 9/2012 |
| WO | 91/16020 A1 | 10/1991 |
| WO | 2004/058081 A1 | 7/2004 |
| WO | 2008/024937 A2 | 2/2008 |
| WO | 2008/119006 A1 | 10/2008 |
| WO | 2009/073655 A1 | 6/2009 |
| WO | 2010/056846 A2 | 5/2010 |
| WO | 2011/059732 A1 | 5/2011 |
| WO | 2011/109009 A1 | 9/2011 |
| WO | 2011/127065 A1 | 10/2011 |
| WO | 2012/024665 A2 | 2/2012 |
| WO | 2012/030712 A1 | 3/2012 |
| WO | 2012/035479 A2 | 3/2012 |
| WO | 2012/060868 A1 | 5/2012 |
| WO | 2013/028851 A1 | 2/2013 |

OTHER PUBLICATIONS

[No Author Listed] A New Angle on Correction. Expedium. DePuy. 2009. 2 pages.
[No Author Listed] Straight Talk with Expedium. Expedium. 10 pages. Jul. 2007.
[No Author Listed] Surgical Technique Guide and Ordering Information. Expedium. DePuy Spine Inc. Sep. 2011. 24 Pages.
[No Author Listed] Value Analysis Brief—Expedium Favored Angle Screw. DePuy Synthes Spine. Aug. 2012. 4 pages.
[No Author Listed] Viper 2 MIS Spine System. System Guide. DePuy Spine Inc. Sep. 2011. 60 pages.
[No Author Listed] Expedium Dual Innie Brochure, DePuy Spine, Aug. 1, 2004.
[No Author Listed] Moss Miami Polyaxial Reduction Screw Surgical Technique, DePuy AcroMed, Inc. 1998.
[No Author Listed] Viper 2 MIS Extended Tab , DePuy Spine, Inc., Feb. 1, 2009.
Duerig, "Engineering Aspects of Shape Memory Alloys", T W Duerig et al, on p. 370, Butterworth-Heinemann (1990).
International Search Report for PCT/US14/021198 mailed Jun. 5, 2014 (3 Pages).
International Search Report and Written Opinion for Application No. PCT/US2013/060350, mailed Jan. 3, 2014 (9 pages).
International Preliminary Report on Patentability for Application No. PCT/US2014/021198, mailed Sep. 24, 2015 (7 pages).
U.S. Appl. No. 61/706,860, filed Sep. 28, 2012 (66 pages).

* cited by examiner

BONE ANCHOR ASSEMBLIES WITH MULTIPLE COMPONENT BOTTOM LOADING BONE ANCHORS

FIELD

The present invention relates to methods and devices for correcting a spine, and in particular to bone anchor assemblies and methods of using the same.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone anchor with a threaded shank that is adapted to be threaded into a vertebra, and a rod-receiving element, usually in the form of a head having opposed U-shaped slots formed therein. The shank and rod-receiving assembly can be provided as a monoaxial assembly, whereby the rod-receiving element is fixed with respect to the shank, a unidirectional assembly, wherein the shank is limited to movement in a particular direction, e.g., within a single plane, or a polyaxial assembly, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism onto the rod-receiving element.

In certain procedures, it is desirable to utilize a bone anchor, such as a bone screw, having a large diameter shank. Large diameter shanks typically require larger heads on the bone screw, which undesirably increases the bone anchor assembly profile. Such large diameter bone screws often utilize a bottom-loading configuration, in which the head of the threaded shank is loaded into an opening in the bottom of the rod-receiving element. This can be done during manufacturing, or intraoperatively either before or after the threaded shank is implanted in bone. This allows the diameter of the shank to remain independent of the size of the opening formed in the rod-receiving element. However, angulation and the ability to perform correctional techniques with such bottom-loading bone anchor assemblies can be limited. Such bone anchor assemblies can break or separate as a result of extreme angulation. This problem is exacerbated with favored-angle bone anchor assemblies, in which a bottom surface of the receiver member is angled such that a cone of angulation of the bone anchor relative to the receiver member is biased in one direction. These devices must be able to withstand tensional forces applied thereto when the rod-receiving element is angulated relative to the shank or during bending of a spinal fixation rod seated therein.

Accordingly, there remains a need for improved devices and methods for correcting a spine, and in particular to improved bottom-loading anchor assemblies and methods.

SUMMARY

Various bone anchor assemblies and methods are provided having a multi-component bone anchor that is configured to allow bottom-loading of the bone anchor into a receiver member during use, and to provide secure fixation between the receiver member and the bone anchor. Such a configuration can be particularly useful with favored-angle bone anchors in which the bottom surface of the receiver member is angled such that a cone of angulation of the bone anchor relative to the receiver member is biased in one direction.

In one embodiment, a bone anchor assembly is provided that includes a bone anchor, such as a bone screw, having a shank with a distal threaded portion and a proximal head portion. The receiver member can define a polyaxial seat. The assembly can further include a non-expandable outer ring configured to be polyaxially disposed within the polyaxial seat of the receiver member and defining a central opening through which the head portion of the shank can be received. The assembly can also include an expandable inner ring having an inner surface configured to mate with the head portion of the shank and an outer surface configured to mate with an inner surface of the outer ring to thereby lock the outer ring in a fixed position relative to the shank.

The receiver member can have a variety of configurations. In one embodiment, the receiver member can include opposed U-shaped cut-outs formed in a proximal portion thereof for receiving a spinal fixation element, such as a spinal rod. In some aspects, the receiver member can have a distal end surface that extends in a plane that is angled relative to a plane of symmetry of the proximal portion to provide a favored-angle seating arrangement. A diameter of the aperture formed in the receiver member can be less than a major diameter of the distal threaded portion of the shank. The bone anchor assembly can also include a compression cap configured to be advanced distally within the receiver member to exert a force on at least one of the inner ring, the outer ring, and the head portion of the shank to thereby lock the shank in a fixed angular orientation relative to the receiver member.

The bone anchor can also have a variety of configurations. In one embodiment, an outer surface of the outer ring can form a portion of a sphere. In some aspects, the outer ring can have an unbroken circumference. The inner ring can also have various configurations, and in one aspect the outer surface of the inner ring is frustoconical and the inner surface of the outer ring is frustoconical such that the inner and outer rings mate by interference fit. In other aspects, the inner ring can include at least one of a slit, a cut, or an opening formed therein such that the inner ring has an adjustable diameter.

A mechanical lock can be formed between the inner ring and the head portion of the shank such that the mechanical lock is configured to substantially prevent axial translation of the inner ring relative to the head portion of the shank. The mechanical lock can include an annular projection formed on one of the head portion of the shank and an inner surface of the inner ring, and a complementary annular groove formed in the other one of the inner surface of the inner ring and the head portion of the shank for seating the annular projection.

In another embodiment, the aperture in the receiver member can be sized and shaped such that the outer ring can be passed proximally through the aperture and into the polyaxial seat in a first orientation in which a longitudinal axis of the central opening of the outer ring is transverse to a longitudinal axis of the aperture, and the outer ring can be rotated within the polyaxial seat to a second orientation in which the longitudinal axis of the central opening of the outer ring is coaxial with the longitudinal axis of the aperture and in which the outer ring cannot be passed distally through the aperture. For example, the aperture can have a shape that comprises a circular central portion with one or more wings extending laterally therefrom, and a maximum diameter of the outer ring can be greater than a diameter of the circular central portion.

Methods of assembling a bone anchor assembly are also provided. In one embodiment, the method can include advancing a head portion of a shank proximally through an aperture formed in a distal end of a receiver member, and advancing the head portion of the shank into a central opening of an outer ring such that an inner ring is captured between the head portion of the shank and the outer ring to lock the position of the shank relative to the outer ring.

The inner ring can be coupled to one of the head portion of the shank and the outer ring prior to advancing the head portion of the shank into the central opening of the outer ring. In one embodiment, the inner ring can be coupled to the head portion of the shank by expanding the inner ring and engaging an annular projection formed on one of the head portion of the shank and an inner surface of the inner ring with a complementary annular groove formed in the other one of the inner surface of the inner ring and the head portion of the shank. In another embodiment, the inner ring can be coupled to the outer ring by an interference fit formed between frustoconical surfaces on the inner and outer rings.

The method can also include advancing a compression cap distally within the receiver member to exert a force on at least one of the inner ring, the outer ring, and the head portion of the shank. In another embodiment, the method can include passing the outer ring proximally through the aperture in a first orientation in which a longitudinal axis of the central opening of the outer ring is transverse to a longitudinal axis of the aperture and then rotating the outer ring to a second orientation in which the longitudinal axis of the central opening of the outer ring is coaxial with the longitudinal axis of the aperture and in which the outer ring cannot be passed distally through the aperture. The method can be performed during manufacturing or intraoperatively.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
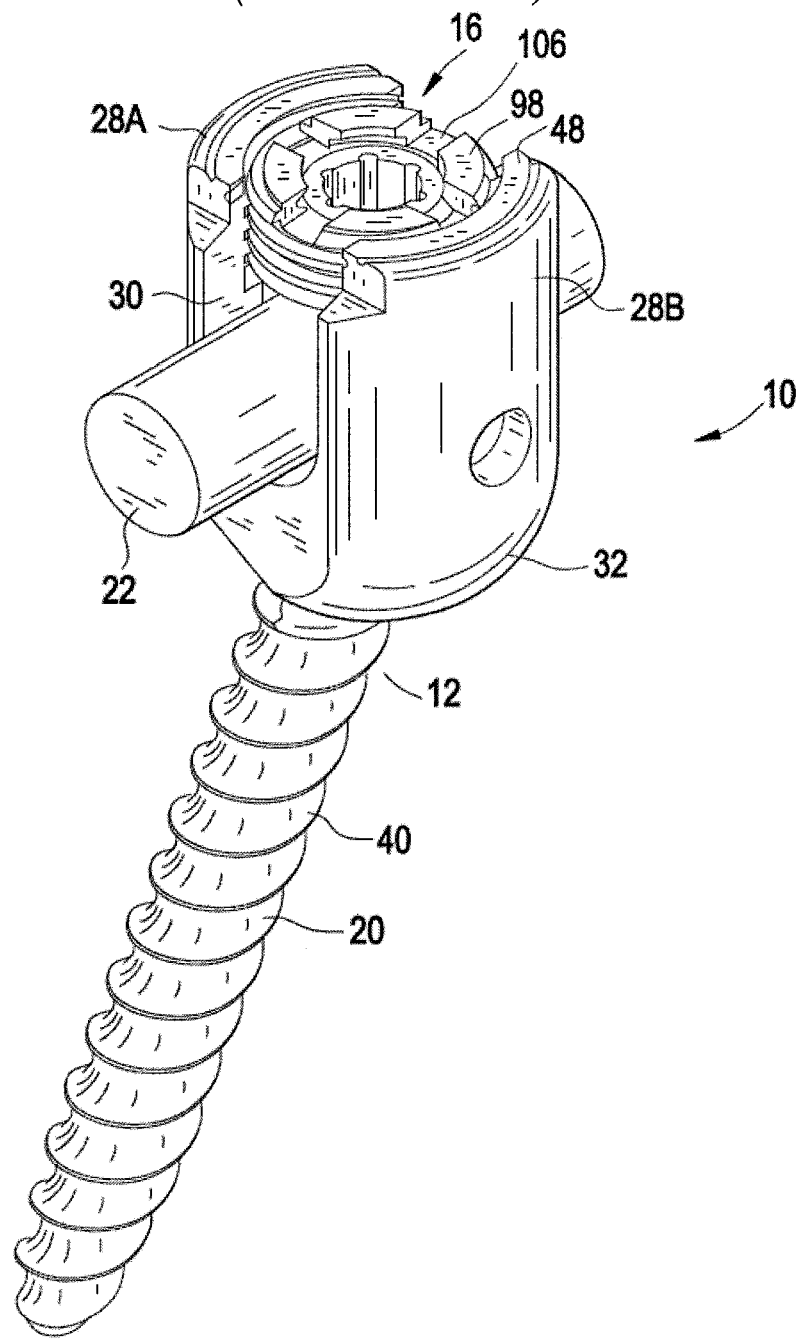
FIG. 1A is a perspective view of a prior art bone anchor assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, various bone anchor assemblies and methods are provided having a multi-component bone anchor that is configured to allow the shank of the bone anchor to be bottom loaded into a receiver member during a procedure. Such devices and methods can allow for the use of bone anchors having large diameter shanks capable of withstanding greater bending forces, while still utilizing a relative low-profile receiver member for coupling a spinal fixation element to the bone anchor. The bone anchor assemblies and methods can also be particularly useful with favored-angle bone anchors in which a cone of angulation of the bone anchor relative to the receiver member is biased in one direction.

FIGS. 1A-1D illustrate a prior art bone anchor assembly 10 that includes a bone anchor 12, a receiver member 14 for receiving a spinal fixation element, such as a spinal rod 22, to be coupled to the bone anchor 12, and a closure mechanism 16 to capture the spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 and the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2011/0288599, filed on Aug. 22, 2012, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly 10, including, for example, the closure mechanism 16, the receiver member 14, and the compression member 60 (discussed below) can be cannulated or otherwise have an opening to permit delivery over a guide wire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyapatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 14 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member 14 and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 14. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member 14.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can include an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 72 can include drive features for receiving an instrument to rotate and advance the inner set screw 72 relative to the outer set screw 74. The illustrated inner set screw 72 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae In use, bone can be prepared to receive the bone anchor assembly 10, generally by drilling a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into the prepared hole in the bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the outer set screw 70 to move it within the recess 30 using a tool which can engage the plurality of cut-outs 106 in the upper facing surface of the outer set screw 70, so as to force the compression member 60 onto the proximal head 18 of the bone anchor 12. Torsional forces can then be applied to the inner set screw 72 to move it relative to the outer set screw 70 so that it contacts the spinal rod 22 and can, for example, fix the spinal rod 22 relative to the receiver member 14 and the bone anchor 12.

One or more embodiments of inventive bone anchor assemblies are described below. Except as indicated below, the structure, operation, and use of these embodiments is similar or identical to that of the bone anchor assembly 10 described above. Accordingly, a detailed description of said structure, operation, and use is omitted here for the sake of brevity.

Figure 1B:
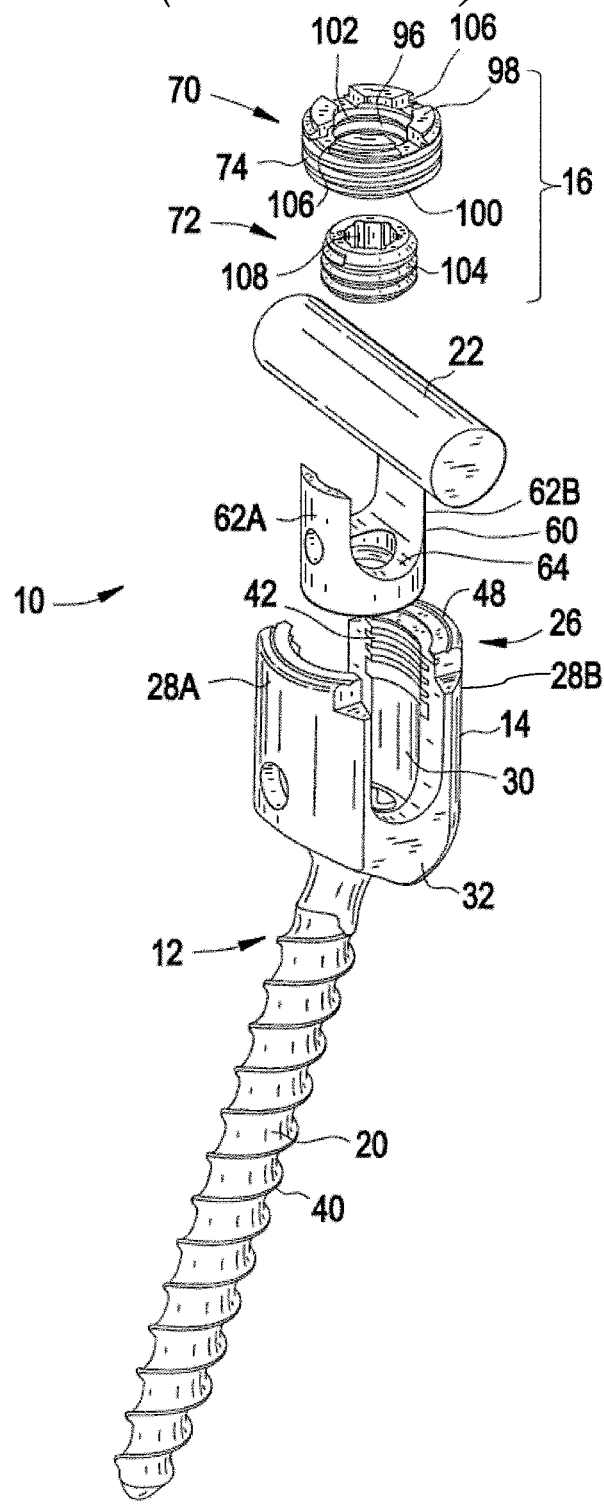
FIG. 1B is an exploded view of the bone anchor assembly of FIG. 1A.
Figure 1C:
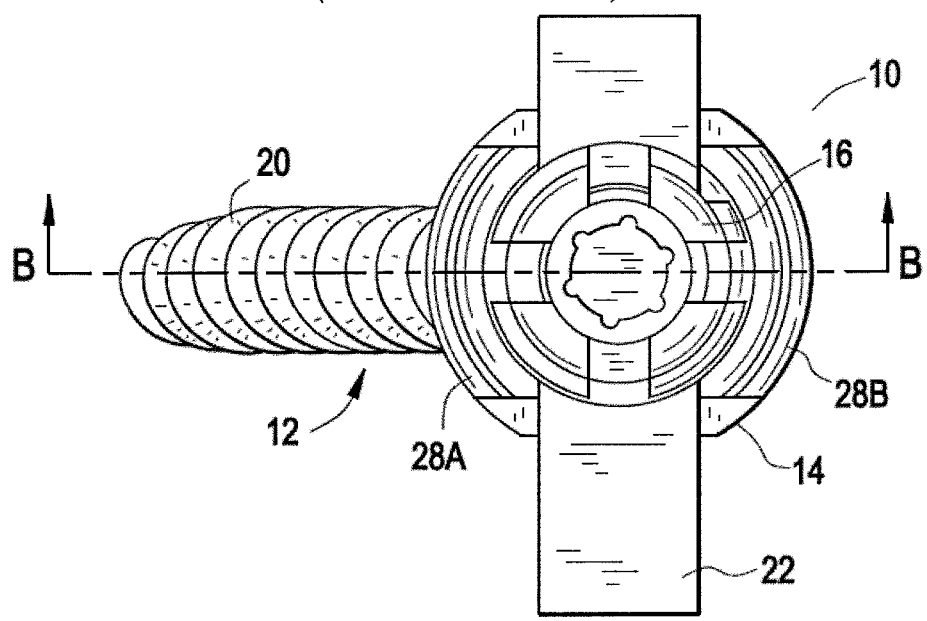
FIG. 1C is a top view of the bone anchor assembly of FIG. 1A.
Figure 1D:
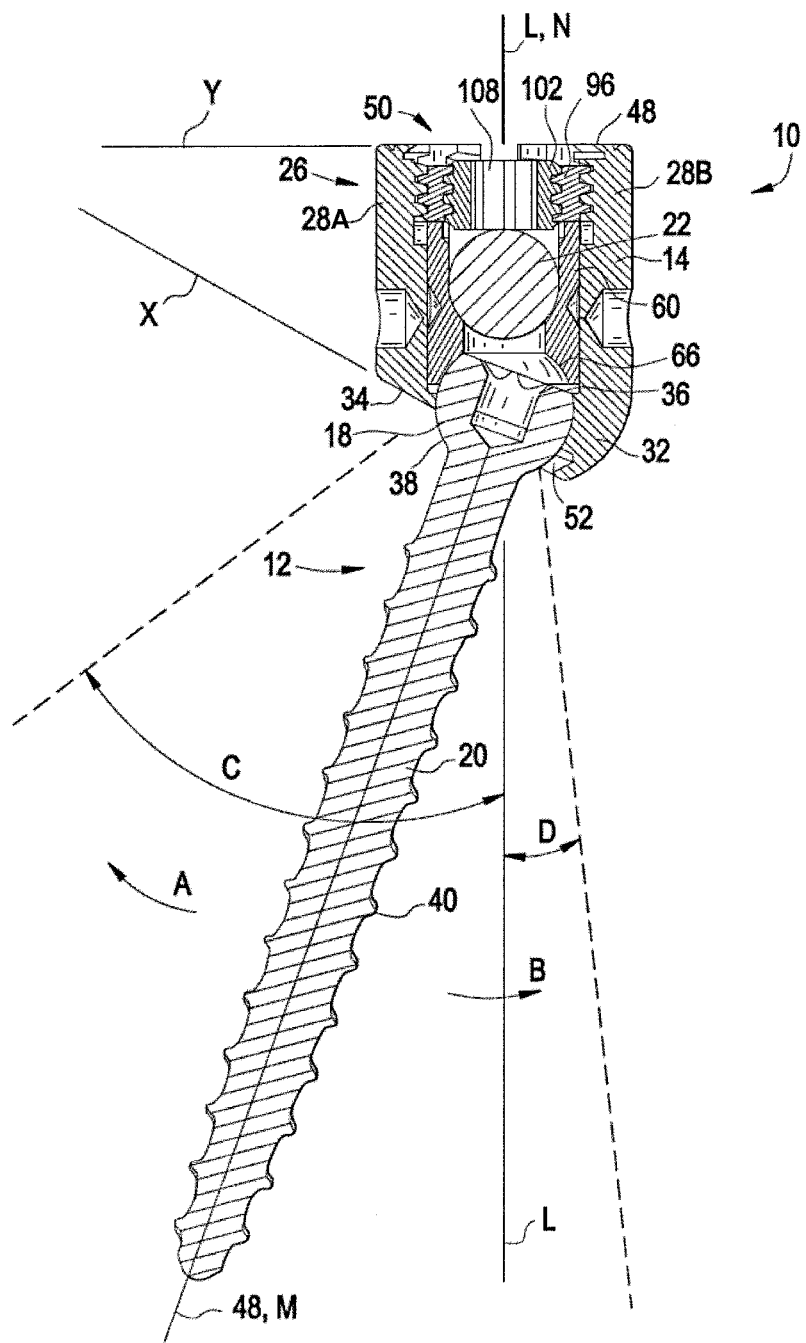
FIG. 1D is a cross-sectional view of the bone anchor assembly of FIG. 1A.
Figure 2:
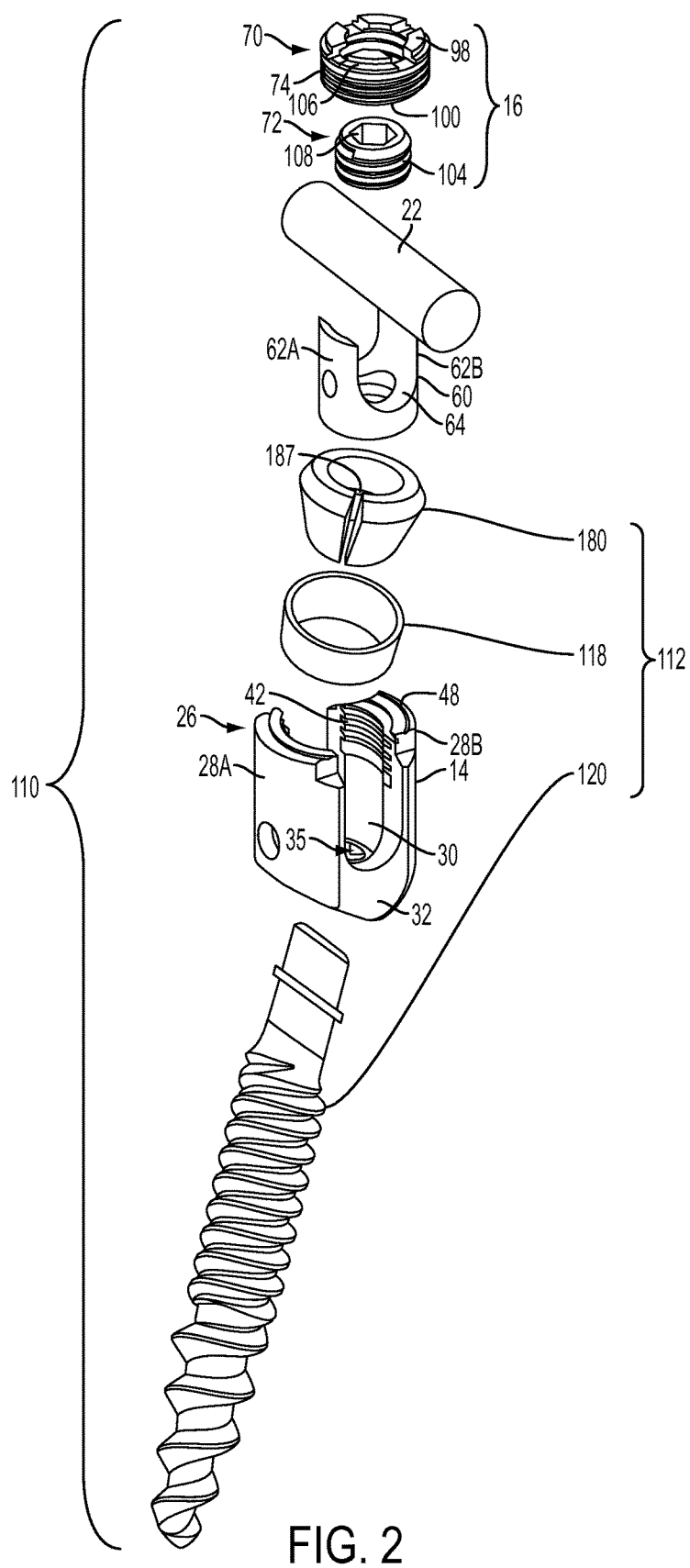
FIG. 2 is an exploded view of a bone anchor assembly including a multi-part bone anchor.
Figure 3A:
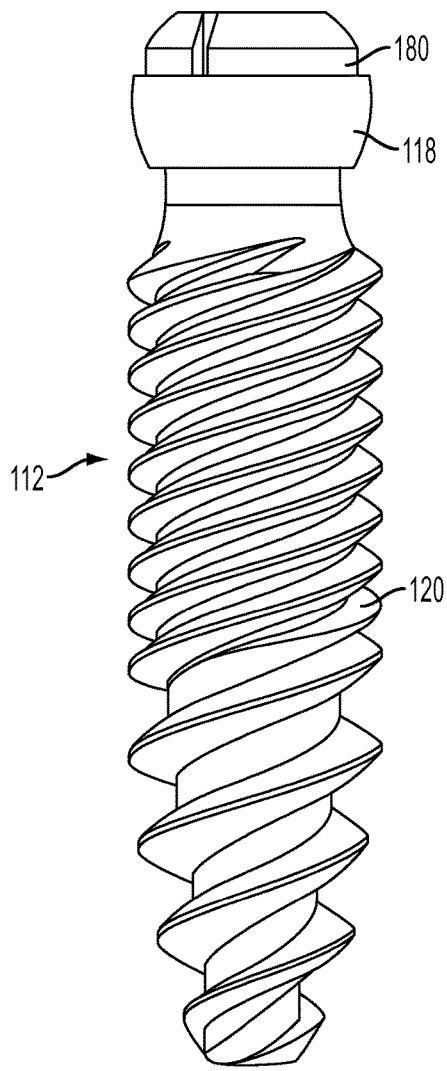
FIG. 3A is a side view of the bone anchor of FIG. 2.
Figure 3B:
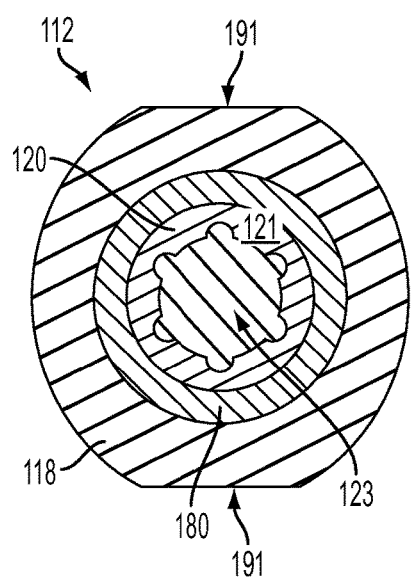
FIG. 3B is a top view of the bone anchor of FIG. 2.

FIG. 2 illustrates a bone anchor assembly 110 that is similar to the bone anchor assembly 10 shown in FIGS. 1A and 1B, except that the bone anchor assembly 110 includes a multi-component bone anchor. As shown in FIG. 2, the bone anchor includes a shank 120 configured to engage bone, an outer ring 118, and an inner ring 180. As shown in FIGS. 3A and 3B, the inner ring 180 is configured to mate the outer ring 118 to the shank 120 in an assembled configuration. During manufacturing or during a surgical procedure, either before or after the shank 120 is implanted, the shank 120 can be proximally advanced, e.g., bottom-loaded, into the receiver member 14 and then mated to the outer ring 118 by the inner ring 180. The outer ring 118 of the bone anchor can be polyaxially seated within a polyaxial seat in the receiver member 14 in a ball and socket like arrangement such that the outer ring 118 and the shank 120 can pivot relative to the receiver member 14. The inner ring 180 will lock the outer ring 118 onto the shank 120 such that the shank 120 is mated to the receiver member 14. The shank 120 can be polyaxially moved relative to the receiver member 14, and once in a desired position a closure mechanism can be applied to the receiver member to lock a spinal fixation element, such as a spinal rod, therein and to also lock the receiver member 14 in a fixed position relative to the shank 120.

Figure 4:
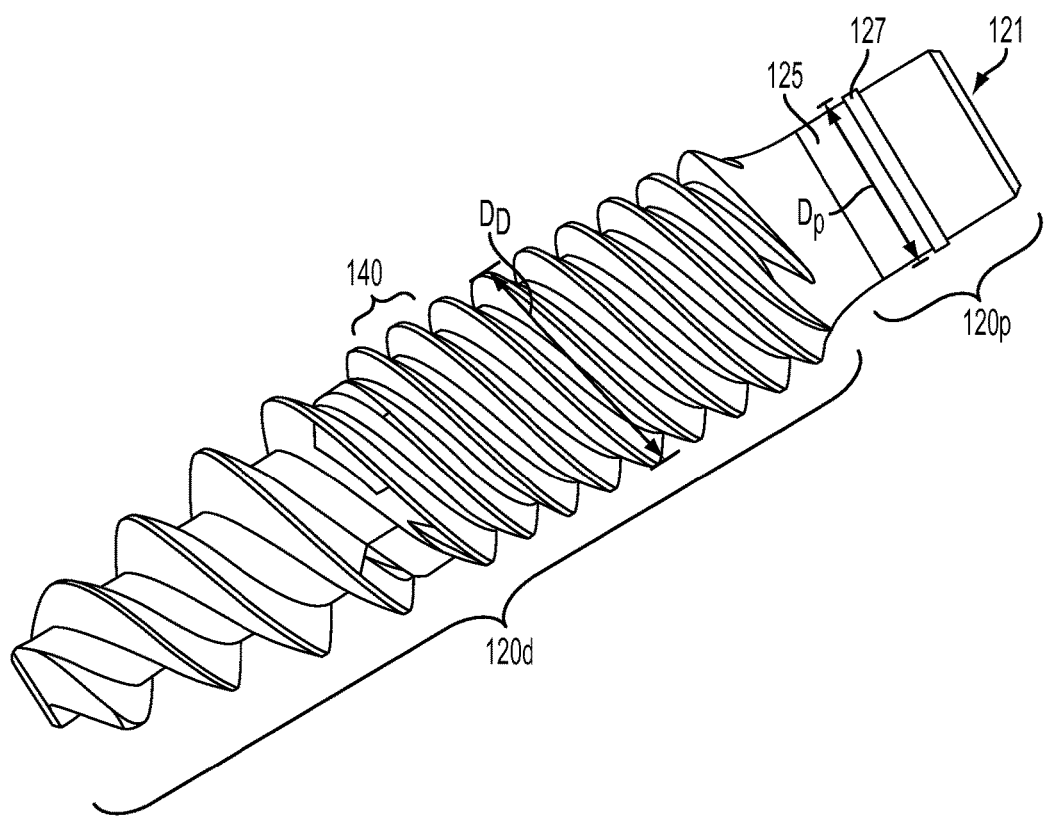
FIG. 4 is a side view of the shank of FIG. 2.

The shank 120 is illustrated in more detail in FIG. 4, and as shown the elongate shank 120 of the bone anchor includes a proximal head portion 120p and a distal bone-engaging portion 120d. In this embodiment, the distal bone-engaging portion 120d is in the form of a threaded shank having an external bone engaging thread 140, and the proximal portion 120p is thread-free and is in the form of a head. While the proximal portion 120p can have various shapes and sizes, in an exemplary embodiment the proximal portion 120p is generally cylindrical and has a major diameter $D_P$ that is less than a major diameter $D_D$ of the distal portion 120d. The proximal portion 120p of the shank 120 can also have a major diameter $D_P$ that is less than a diameter $D_R$ (not shown) of an opening or aperture 35 in a distal end 32 of the receiver member 14 such that the proximal portion 120p of the shank 120 can be received through the aperture 35. Conversely, the distal portion 120d of the shank 120 can have a major diameter $D_D$ that is greater than the diameter $D_R$ (not shown) of the aperture 35 in the receiver member 14 such that the distal portion 120d of the shank 120 is prevented from passing through the aperture 35. Such a configuration can allow the proximal portion 120p of the shank 120 to be proximally advanced through the aperture 35 in the distal end of the receiver member 14, i.e., "bottom loaded" into the receiver member. A person skilled in the art will appreciate, however, that the shank 120 need not have a major diameter $D_D$ that is greater than the diameter of the aperture 35 in the receiver member 14, and any sized shank can be used with the present invention. As further shown in FIG. 4, the proximal portion 120p of the shank 120 can also have a substantially planar proximal surface 121 that can optionally include a tool receiving recess 123 therein (see FIG. 3B).

As further shown in FIG. 4, the substantially cylindrical sidewall 125 of the proximal portion 120p can include a feature configured to form a mechanical lock with the inner ring 180, discussed further below, so as prevent axial translation of the inner ring 180 with respect to the shank 120 when mated together. In the illustrated embodiment, the feature is in the form of an annular projection 127 formed on the proximal portion 120p of the shank and that is configured to fit within a complementary annular groove 187 formed in the inner ring 180, as discussed further below. It will be understood that, alternatively, a mechanical lock can be formed by having a groove formed in the shank and a complementary projection formed on the inner ring, or any other type of mechanical lock. The location of the annual projection 127 can vary, but it is preferably disposed at a location along the proximal portion 120p that is configured to retain the outer ring 118 in a position such as that shown in FIG. 3A. In an exemplary embodiment, the annual projection 127 is located at an intermediate position between proximal and distal ends of the proximal portion 120p.

Figure 5:
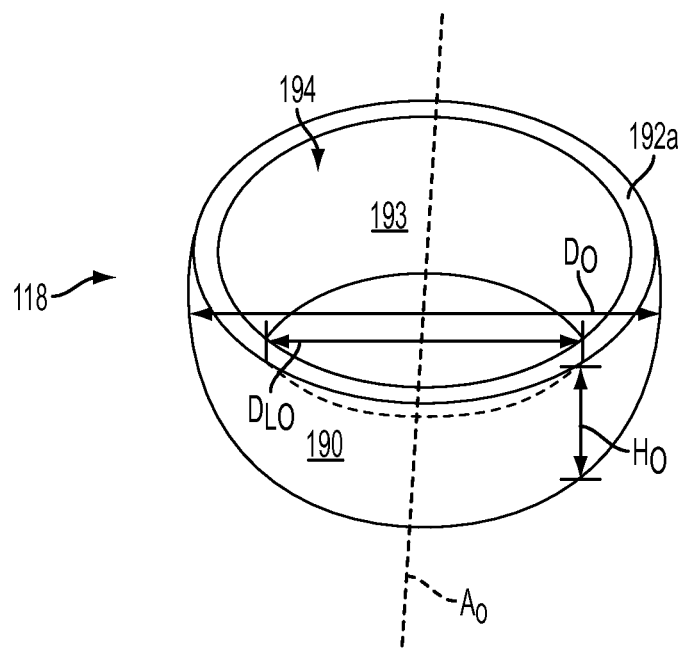
FIG. 5 is a perspective view of the outer ring of FIG. 2.

FIG. 5 illustrates the outer ring 118 in more detail. The outer ring 118 is configured to receive the proximal portion 120p of the shank 120 therein and to retain the shank 120 within the receiver member 14. While the outer ring 118 can have a variety of configurations, in an exemplary embodiment the outer ring 118 is at least partially spherical to allow the outer ring 118 to be seated within a spherical recess (not shown) formed within the receiver member 14 to form a ball and socket like arrangement to allow the shank 120 to pivot relative to the receiver member 14. In the illustrated embodiment, the outer ring 118 is non-expandable so as to prevent the outer ring 118 from deforming and detaching from the shank 120 when the bone anchor is coupled to the receiver member 14. In particular, the outer ring 118 can be solid with an unbroken circumference, having no slits or cuts formed therein such that it does not bend, compress, or expand. The outer ring 118 can be shaped like a truncated sphere with a substantially spherical outer surface 190 and substantially planar top and bottom surfaces 192a (bottom surface not shown). While the spherical exterior surface 190 can provide for a full range of polyaxial motion, in other embodiments, the substantially spherical outer surface 190 can include one or more flat portions 191 (see FIG. 3B) that correspond to flat portions of the receiver member such that angulation of the bone anchor is limited to a single plane.

The dimensions of the outer ring 118 can vary, but in an exemplary embodiment the outer ring 118 has a maximum diameter $D_O$ that is greater than a diameter of the aperture 35 in the distal end 32 of the receiver member 14. However, in some embodiments, as discussed below, the receiver member can have an aperture sized and shaped such that the outer ring can be passed through the aperture in one orientation and prevented from passing through in a different orientation. The outer ring 118 can also have a height $H_O$ that can vary, but the height $H_O$ is preferably less than a height of the receiver member 14 and is equal to or less than a height of the proximal portion 120p of the shank 120.

As further shown in FIG. 5, the outer ring 118 can also include an inner surface 193 that defines a lumen or bore 194 formed through the outer ring 118 and extending between the top and bottom surfaces 192a, 192b along a longitudinal axis $A_O$. The bore 194 can be configured to receive the proximal portion 120p of the shank 120 and the inner ring 180. The shape of the bore 194 can vary, but the bore is preferably configured to form an interference fit with the inner ring 180. In the illustrated embodiment, the inner surface 193 defines a generally frustoconical bore 194 that is configured to complement the shape of the inner ring 180, discussed below. The frustoconical bore 194 can increase in diameter from a distal end to a proximal end of the outer ring 118. It will be understood that the bore can have various other shapes, such as cylindrical, spherical, hourglass, or double cone, for example. The size of the bore 194 can also vary, but preferably the bore 194 has a diameter $D_{LO}$ that is sized to provide an interference fit with the inner ring 180.

Figure 6:
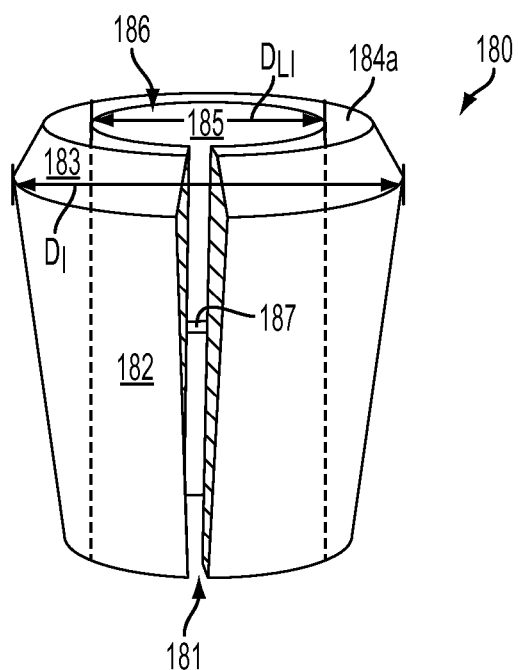
FIG. 6 is a perspective view of the inner ring of FIG. 2.
Figure 7:
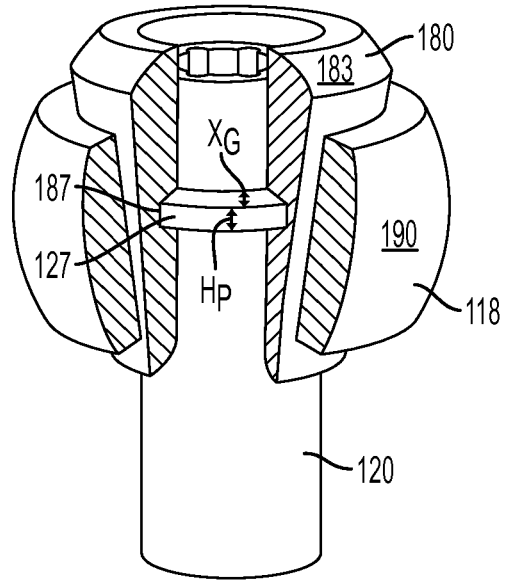
FIG. 7 is a partial sectional view of the bone anchor of FIG. 2.
Figure 8:
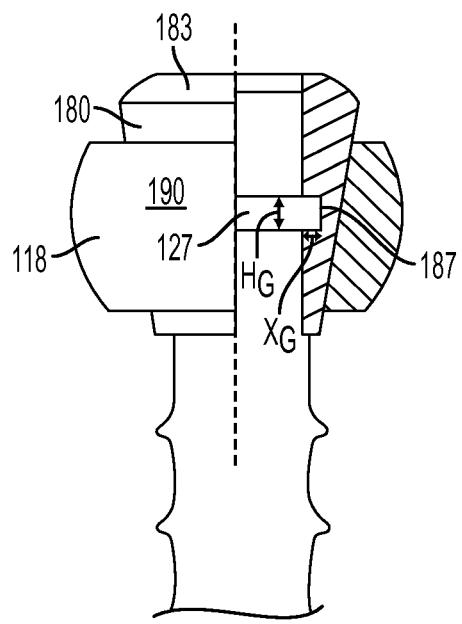
FIG. 8 is a partial sectional view of the bone anchor of FIG. 2.

FIG. 6 illustrates the inner ring 180 in more detail. The inner ring 180 can be configured to mate to both the shank 120 and the outer ring 118. As shown in FIG. 6, the inner ring 180 can have a frustoconical outer surface 182, substantially planar top bottom surfaces 184a (bottom surface not shown), and a lumen 186 extending therethrough that defines an inner surface 185. The inner ring can also include a slit 181 extending longitudinally therethrough from the outer surface 182 to the inner surface 185 to allow the inner ring to expand and contract, as shown in FIG. 6. However, in some embodiments as discussed further below, the flexible inner ring does not need to have a slit. The inner ring 180 can also include a tapered or spherical surface 183 that extends from the planar top surface 184a to the frustoconical outer surface 182. The spherical surface 183 can form a continuation of the spherical outer surface 190 of the outer ring 118. In some embodiments, the spherical surface 183 of the inner ring 180 and the spherical outer surface 190 of the outer ring 118 can form a substantially continuous spherical surface (see FIG. 9B) when mated. However, in other embodiments, such as shown in FIGS. 3A, 7, and 8, the spherical surface 183 of the inner ring 180 and the spherical outer surface 190 of the outer ring 118 can share a common center point and can form an interrupted spherical surface.

As indicated above, the frustoconical outer surface 182 of the inner ring 180 can complement the frustoconical inner surface 193 of the outer ring 118 so as to allow the inner and outer rings 180, 118 to mate by interference fit. Thus, the outer surface 182 can increase in diameter from a distal end to a proximal end of the inner ring 180. As the inner ring 180 is distally advanced into the proximal end of the outer ring 118, the frustoconical configuration will allow the inner ring 180 frictionally engage the outer ring 118 so as to form an interference fit. In particular, the inner ring 180 preferably has a maximum outer diameter $D_I$ that is less than a maximum inner diameter $D_{LO}$ of the outer ring 118 such that the inner ring 180 cannot pass fully through the outer ring 118, and so as to result in an interference fit between the two components. The position at which the interference fit is formed can vary and, as indicated above, it can be configured such that together the inner and outer rings 180, 118 form a continuous or an interrupted spherical outer surface.

The lumen 186 extending through the inner ring 180 between the top and bottom surfaces 184a (bottom surface not shown) can be configured to receive the proximal portion 120p of the shank 120 therethrough. While the shape of the lumen can vary, in the embodiment shown in FIG. 6 the lumen 186 is generally cylindrical to complement the shape of the proximal portion 120p of the shank 120.

The lumen 186 in the inner ring 180 can also include a feature to allow the inner ring 180 to be fixedly mated to the shank 120. In one embodiment, shown in FIGS. 6, 7, and 8, the inner surface 185 can include a mechanical lock, such as an annular groove 187 or an annular projection, formed thereon. The annular groove 187 can be configured to receive the complementary annular projection 127 on the shank 120. While the annular groove 187 can have a height and a depth greater than or equal to the height and the depth of the annular projection, the height $H_G$ and the depth $X_G$ of the groove 187 can be substantially equal to the height $H_P$ and the depth $X_P$ of the projection 127, as shown in FIGS. 7 and 8, such that axial translation of the shank 120 is prevented with respect to the inner ring 180 when the projection 127 is engaged by the groove 187.

Figure 9A:
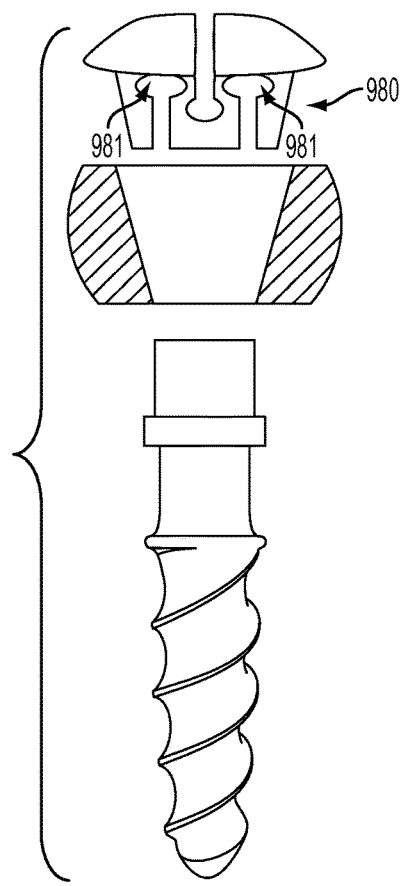
FIG. 9A is an exploded view of another embodiment of a multi-part bone anchor.
Figure 9B:
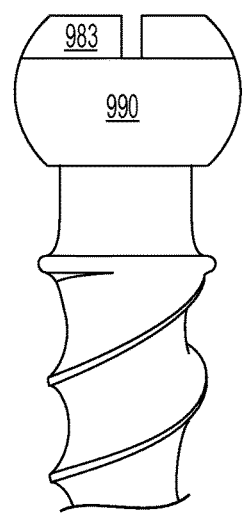
FIG. 9B is a side view of the bone anchor of FIG. 9A.

As indicated above, the inner ring 180 can also include a slit 181 for allowing the inner ring 180 to expand and contract such that a maximum outer diameter $D_I$ of the inner ring 180 is adjustable, i.e., can increase or decrease. For example, the outer diameter $D_I$ can increase when the shank 120 is received in the lumen 186 of the inner ring 180, or the diameter $D_I$ can decrease when the inner ring 180 is drawn into the outer ring 118. The inner ring 180 can return to an original resting state, or it can be slightly expanded, when the annular projection 127 on the proximal portion 120p of the shank 120 is seated within the annular groove 187 in the inner ring 180. As also indicated above, the maximum outer diameter $D_I$ of the inner ring 180 can be greater than the minimum diameter $D_{LO}$ of the bore 194 of the outer ring 118 such that the inner ring 180 is prevented from fully passing through the outer ring 118. Instead, the inner ring 180 can wedge between the outer ring 118 and the shank 120 such that the outer ring 118 and the shank 120 are locked in fixed engagement with one another. As shown in FIG. 6, the slit 181 can be a single vertical slit that extends from the top surface 184a of the inner ring 180 to the opposed bottom surface (not shown). In other embodiments, the slit can be one or more slits, cuts, openings, or cut-outs formed in the inner ring. For example, FIG. 9A shows another embodiment of an inner ring 980 that is a unitary, continuous member with a plurality of cut-outs 981 that extend therethrough. The cut-outs can have a shape defined by an open rectangular portion and a circular portion.

Figure 9C:
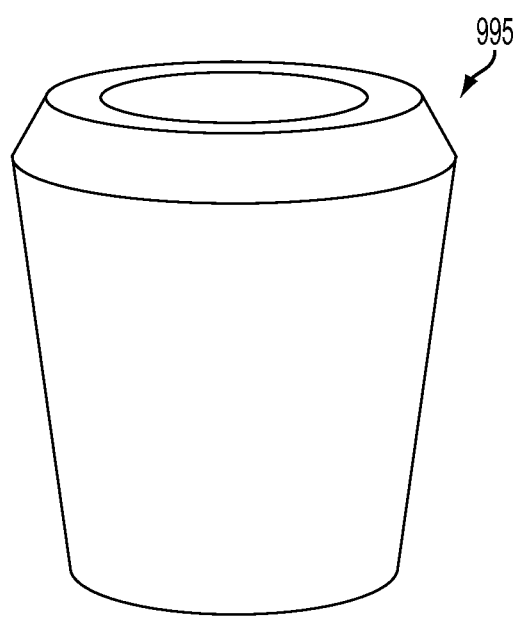
FIG. 9C is a perspective view of another embodiment of an inner ring.

In another embodiment, as indicated above, the inner ring can be slit-free while still being flexible such that an outer diameter of the inner ring and a diameter of the bore are adjustable. For example, as shown in FIG. 9C, the inner ring 995 can have an uninterrupted circumference and a continuous outer surface. In an exemplary embodiment, the inner ring 995 can be formed from an expandable material such that the inner ring can expand and/or contract when a force is applied thereto. Exemplary materials include, by way of non-limiting example, shape memory alloys, such as nitinol, and any material that has elastic properties. In another exemplary embodiment, the inner ring can heated and/or cooled such that the outer diameter or the diameter of the bore can be adjusted.

Figure 10:
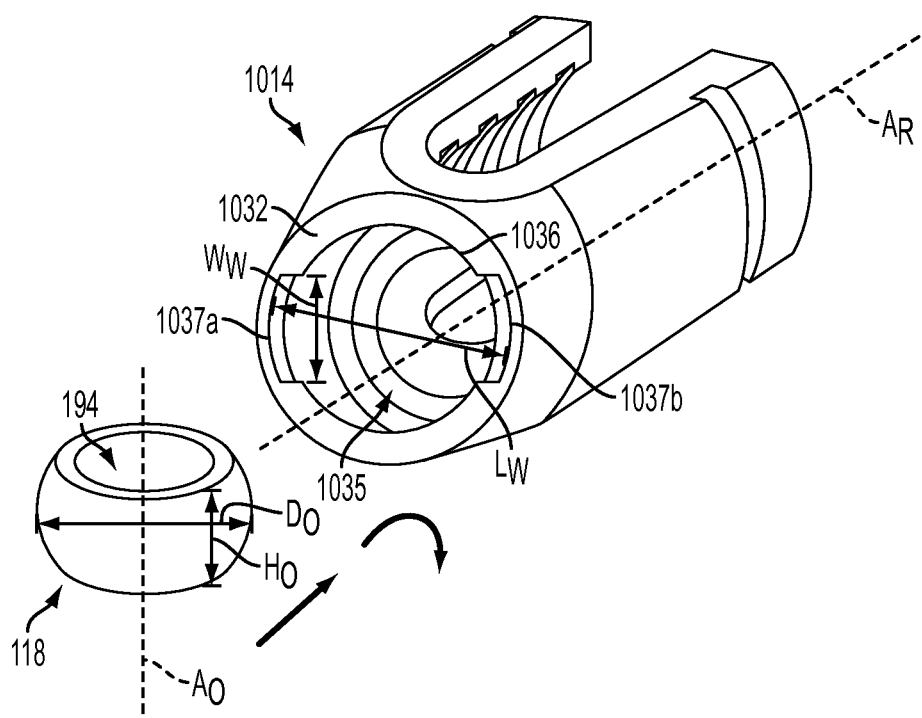
FIG. 10 is a perspective view of another embodiment of a receiver member and the outer ring of FIG. 2.

The bone anchor can be used with prior art receiver members as discussed above, or, alternatively, the bone anchor can be used with a receiver member 1014 as shown in FIG. 10. As mentioned above, the receiver member can have an aperture sized and shaped such that the outer ring can be passed through the aperture in certain orientations. For example, the receiver member 1014 can include a distal end 1032 having an aperture 1035 extending therethrough and communicating with a polyaxial seat formed in the receiver member 1014. The aperture 1035 can have a central longitudinal axis $A_R$ and a circular central portion 1036 with a diameter $D_C$ that is less than the outer diameter $D_O$ of the outer ring 118. The diameter $D_C$ of the central portion 1036 can increase distally such that a range of motion of a bone anchor extending therethrough is increased. The aperture 1035 can also include opposed lateral wings 1037a, 1037b that extend from the central portion 1036 transverse to the axis $A_R$. The lateral wings 1037a, 1037b can have a combined length $L_W$ that is greater than the outer diameter $D_O$ of the outer ring 118 and a width $W_W$ that is greater than the height $H_O$ of the outer ring such that, when the outer ring 118 is oriented with the axis $A_O$ transverse to the axis $A_R$ of the receiver member 1014, the outer ring 118 can be passed proximally through the aperture 1035 and into the polyaxial seat on the proximal surface of the distal end 1032 of the receiver member 1014. When rotated such that the axis $A_O$ is parallel to the axis $A_R$ of the receiver member 1014, the outer ring 118 is prevented from passing distally through the aperture 1035 and therefore is retained within the seat in the receiver member 1014. The lateral wings 1037a, 1037b can allow greater angulation of a bone anchor with respect to the receiver member 1014 in a plane of the lateral extensions 1037a, 1037b.

Figure 11:
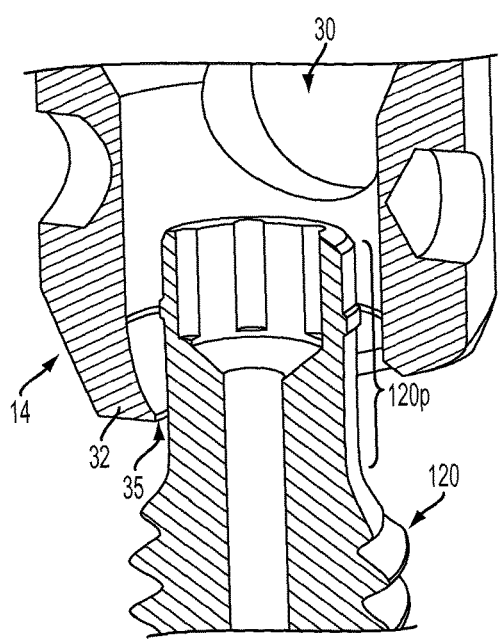
FIG. 11 illustrates a shank inserted in a distal end of a receiver member.
Figure 12:
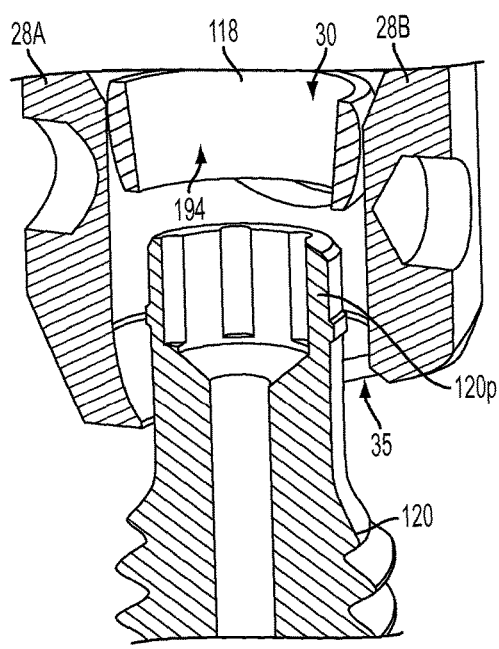
FIG. 12 illustrates an outer ring inserted into the receiver member of FIG. 11.
Figures 13, 14:
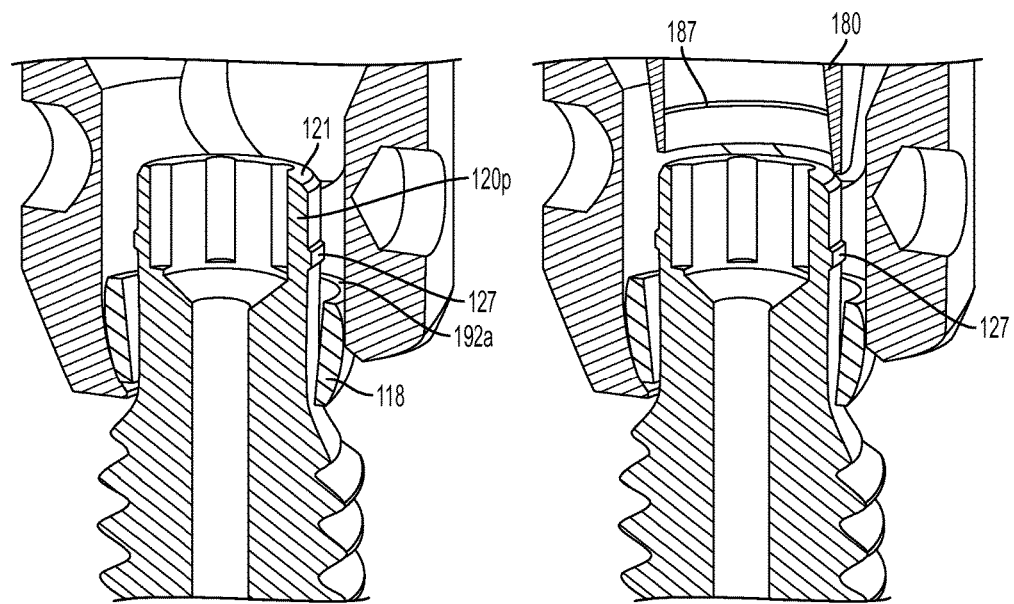
FIG. 13 illustrates the shank inserted proximally through the outer ring of FIG. 12.
FIG. 14 illustrates an inner ring inserted into the receiver member of FIG. 13.
Figure 15:
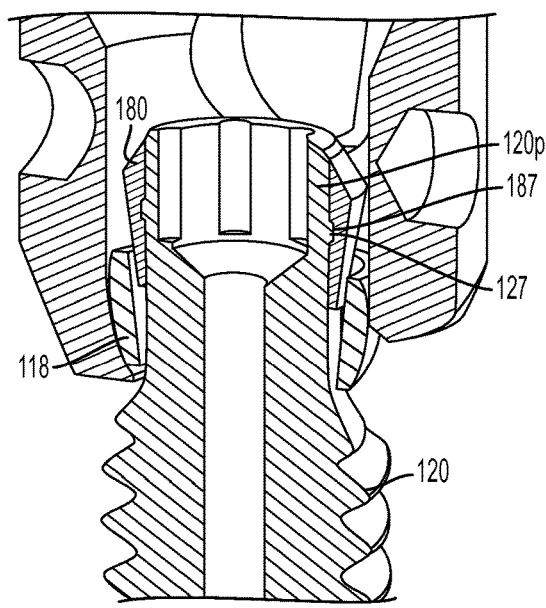
FIG. 15 illustrates the shank engaged with the inner ring of FIG. 14.
Figure 16:
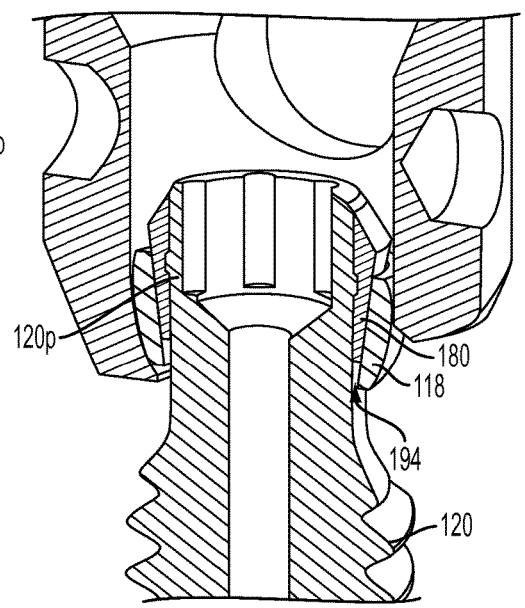
FIG. 16 illustrates the inner ring wedged between the shank and the outer ring of FIG. 15.

In use, the bone anchor assembly 110 can be assembled during manufacturing, before surgery, or intraoperatively. An exemplary method of assembling a bone anchor is illustrated in FIGS. 11-17. While the method is shown in connection with the bone anchor assembly 110 of FIG. 2, the method can be used with any of the bone anchor assemblies disclosed herein. As shown in FIGS. 11-13, the proximal portion 120p of the shank 120 can be proximally advanced through the aperture 35 in the distal end 32 of the receiver member 14 and through the bore 194 of the outer ring 118 in the receiver member 14. The outer ring 118 can already be seated within the recess 30 of the receiver member 14 when the shank 120 is advanced through the aperture 35, or, alternatively, as illustrated by FIGS. 11-13, the outer ring 118 can be placed within the recess 30 after the proximal portion 120p is advanced through the aperture 35. In one embodiment, the outer ring 118 can be top-loaded into the receiver member 14, as shown in FIG. 12. Alternatively, in some embodiments, as discussed with respect to FIG. 10, the outer ring 118 can be bottom loaded through the aperture 1035 as indicated by the arrow while the outer ring 118 is in a first orientation such that the axis $A_O$ of the bore 194 is transverse to the axis of the aperture $A_R$, and, once loaded into the receiver member 14, the outer ring 118 can be rotated to a second orientation so that the axis $A_O$ of the bore 194 is coaxial with the axis of the aperture $A_R$ such that the outer ring 118 cannot be passed through the aperture 1035. Once the outer ring 118 is in the recess 30, the proximal portion 120p of the shank 120 can be advanced such that the proximal surface 121 is proximal to the proximal surface 192a of the outer ring 118. As shown in FIG. 13, the annular projection 127 can be disposed proximal to the outer ring 118. The inner ring 180 can be mated to the proximal portion 120p of the shaft 120 by engaging the annular projection 127 with the complementary annular groove 187, as shown in FIG. 15. The diameter $D_I$ of the inner ring 180 can be expanded to receive the shaft 120 within the lumen 186 thereof. The mated combination of the inner ring 180 and the shaft 120 can be advanced distally into the lumen 194 of the outer ring 118 such that the inner ring 180 becomes wedged between the outer ring 118 and the proximal portion 120p of the shaft 120 and the outer ring 118 and the shaft 120 are in a substantially fixed relationship with each other, as illustrated by FIG. 16. The projection 127 and annular groove 187 form a mechanical interlock that locks the proximal portion 120p of the shank into the inner ring 180, and the outer surface of the inner ring 180 and the inner surface of the outer ring 118 form an interference fit that locks the outer ring 180 onto the shank 120. Since the outer ring 118 is sized to prevent being passed through the aperture in the receiver member 14, the shank 120 is maintained within the receiver member 14. The multi-component bone anchor thus allows for assembly using a bottom loading technique. This can be particularly advantageous with large diameter shanks that are not sized to be distally advanced through the proximal end of the receiver and through the aperture in the receiver member. The secure mating connection between the components also allows the outer ring 118 to be sized so as to prevent passage through the aperture in the receiver member, even when the shank 120 is fully angled to the maximum angulation allowed for with the illustrated favored-angle bone anchor assembly.

Figure 17:
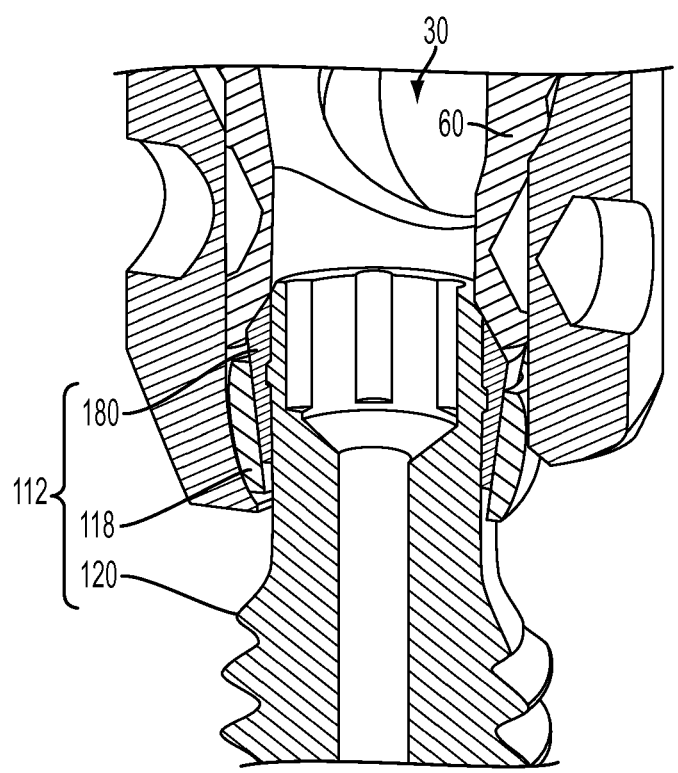
FIG. 17 illustrates a compression cap seated in the receiver member of FIG. 16.

The bone anchor can be implanted in bone, either before or after coupling the receiver member 14 to the shank 120, using a driver tool fitted with the bone anchor. A compression member 60, if utilized, can be positioned within the receiver member such that the arms 62A, 62B of the compression member 60 are aligned with the arms 28A, 28B of the receiver member 14 and the distal-facing surface of the compression member 60 is in contact with the bone anchor. The compression member can exert a frictional force on part of the bone anchor, e.g, the outer ring 118, the inner ring 180, and/or the shank 120, as shown in FIG. 17 to maintain the shank 120 in a desired orientation relative to the receiver member 14, while still allowing movement of the shank 120 with respect to the receiver member 14.

Once the bone anchor is implanted in bone and the receiver member 14 is attached thereto, the receiver member 14 can be pivoted or angulated relative to the bone anchor. One or more bone anchor assemblies (not shown) can also be deployed into bone using the same or different techniques. A spinal fixation element, e.g. the spinal rod 22, can be positioned in the recess 30 of the receiver member 14 and can be manipulated in various ways using various tools so that the spinal rod 22 extends through one or more bone anchor assemblies. Manipulating the spinal rod 22 can change an angle of the receiver member 14 relative to the bone anchor. When the spinal rod 22 is in a desired position, a closure mechanism 16 can be engaged with the inner thread provided on the arms 28A, 28B of the receiver member 14. The closure mechanism 16 can fix the spinal rod 22 relative to the bone anchor assembly 110, and also cause the compression member 60 to engage part of the bone anchor, e.g, the outer ring 118, the inner ring 180, and/or the shank 120, to lock the receiver member 14 in a fixed position relative to the shank 120.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A bone anchor assembly, comprising:
   a shank having a distal threaded portion and a proximal head portion;
   a receiver member having an aperture formed in a distal end thereof through which the head portion of the shank can be received, the receiver member defining a polyaxial seat;
   a non-expandable outer ring configured to be polyaxially disposed and polyaxially movable within the polyaxial seat of the receiver member and defining a central opening through which the head portion of the shank can be received; and
   an expandable inner ring having an inner surface configured to mate with the head portion of the shank and an outer surface configured to mate with an inner surface of the outer ring to thereby lock the outer ring in a fixed position relative to the shank,
   wherein the outer surface of the outer ring forms a portion of a sphere such that the outer ring can polyaxially move within the receiver member.

2. The assembly of claim 1, wherein the outer surface of the inner ring is frustoconical and the inner surface of the outer ring is frustoconical such that the inner and outer rings mate by interference fit.

3. The assembly of claim 1, wherein the inner ring includes at least one of a slit, a cut, and an opening formed therein such that the inner ring has an adjustable diameter.

4. The assembly of claim 1, wherein the receiver member includes opposed U-shaped cut-outs formed in a proximal portion thereof for receiving a spinal fixation rod.

5. The assembly of claim 1, further comprising a mechanical lock between the inner ring and the head portion of the shank such that the mechanical lock is configured to substantially prevent axial translation of the inner ring relative to the head portion of the shank.

6. The assembly of claim 5, wherein the mechanical lock comprises an annular projection formed on one of the head portion of the shank and the inner surface of the inner ring, and a complementary annular groove formed in the other one of the inner surface of the inner ring and the head portion of the shank for seating the annular projection.

7. The assembly of claim 1, further comprising a compression cap configured to be advanced distally within the receiver member to exert a force on at least one of the inner ring, the outer ring, and the head portion of the shank to thereby lock the shank in a fixed angular orientation relative to the receiver member.

8. A bone anchor assembly, comprising:
a shank having a distal threaded portion and a proximal head portion;
a receiver member having an aperture formed in a distal end thereof through which the head portion of the shank can be received, the receiver member defining a polyaxial seat;
a non-expandable outer ring configured to be polyaxially disposed and polyaxially movable within the polyaxial seat of the receiver member and defining a central opening through which the head portion of the shank can be received; and
an expandable inner ring having an inner surface configured to mate with the head portion of the shank and an outer surface configured to mate with an inner surface of the outer ring to thereby lock the outer ring in a fixed position relative to the shank,
wherein the outer ring has an unbroken circumference.

9. A bone anchor assembly, comprising:
a shank having a distal threaded portion and a proximal head portion;
a receiver member having an aperture formed in a distal end thereof through which the head portion of the shank can be received, the receiver member defining a polyaxial seat;
a non-expandable outer ring configured to be polyaxially disposed and polyaxially movable within the polyaxial seat of the receiver member and defining a central opening through which the head portion of the shank can be received; and
an expandable inner ring having an inner surface configured to mate with the head portion of the shank and an outer surface configured to mate with an inner surface of the outer ring to thereby lock the outer ring in a fixed position relative to the shank,
wherein a major diameter of the distal threaded portion of the shank is greater than a diameter of the aperture formed in the receiver member.

10. A bone anchor assembly, comprising:
a shank having a distal threaded portion and a proximal head portion;
a receiver member having an aperture formed in a distal end thereof through which the head portion of the shank can be received, the receiver member defining a polyaxial seat;
a non-expandable outer ring configured to be polyaxially disposed and polyaxially movable within the polyaxial seat of the receiver member and defining a central opening through which the head portion of the shank can be received; and
an expandable inner ring having an inner surface configured to mate with the head portion of the shank and an outer surface configured to mate with an inner surface of the outer ring to thereby lock the outer ring in a fixed position relative to the shank,
wherein a distal end surface of the receiver member extends in a plane that is angled relative to a plane of symmetry of the proximal portion to provide a favored-angle seating arrangement.

11. A bone anchor assembly, comprising:
a shank having a distal threaded portion and a proximal head portion;
a receiver member having an aperture formed in a distal end thereof through which the head portion of the shank can be received, the receiver member defining a polyaxial seat;
a non-expandable outer ring configured to be polyaxially disposed and polyaxially movable within the polyaxial seat of the receiver member and defining a central opening through which the head portion of the shank can be received; and
an expandable inner ring having an inner surface configured to mate with the head portion of the shank and an outer surface configured to mate with an inner surface of the outer ring to thereby lock the outer ring in a fixed position relative to the shank,
wherein the aperture is sized and shaped such that the outer ring can be passed proximally through the aperture and into the polyaxial seat in a first orientation in which a longitudinal axis of the central opening of the outer ring is transverse to a longitudinal axis of the aperture, and the outer ring can be rotated within the polyaxial seat to a second orientation in which the longitudinal axis of the central opening of the outer ring is coaxial with the longitudinal axis of the aperture and in which the outer ring cannot be passed distally through the aperture.

12. A bone anchor assembly, comprising:
a shank having a distal threaded portion and a proximal head portion;
a receiver member having an aperture formed in a distal end thereof through which the head portion of the shank can be received, the receiver member defining a polyaxial seat;
a non-expandable outer ring configured to be polyaxially disposed and polyaxially movable within the polyaxial seat of the receiver member and defining a central opening through which the head portion of the shank can be received; and
an expandable inner ring having an inner surface configured to mate with the head portion of the shank and an outer surface configured to mate with an inner surface of the outer ring to thereby lock the outer ring in a fixed position relative to the shank,
wherein the aperture has a shape that comprises a circular central portion with one or more wings extending laterally therefrom, and wherein a maximum diameter of the outer ring is greater than a diameter of the circular central portion.

13. A method of assembling a bone anchor assembly, comprising:
advancing ahead portion of a shank proximally through an aperture formed in a distal end of a receiver member, the shank having a threaded portion that extends distally from the head;
proximally advancing the head portion of the shank into a central opening of an outer ring disposed within the receiver member such that an inner ring engaged between the head portion of the shank and the outer ring locks the position of the shank relative to the outer ring; and
polyaxially rotating a position of the outer ring relative to the receiver member.

14. The method of claim 13, further comprising, prior to advancing, coupling the inner ring to one of the head portion of the shank and the outer ring.

15. The method of claim 14, wherein the inner ring is coupled to the head portion of the shank by expanding the inner ring and engaging an annular projection formed on one of the head portion of the shank and an inner surface of the inner ring with a complementary annular groove formed in the other one of the inner surface of the inner ring and the head portion of the shank.

16. The method of claim 14, wherein the inner ring is coupled to the outer ring by an interference fit formed between frustoconical surfaces on the inner and outer rings.

17. The method of claim 13, further comprising distally advancing a compression cap in the receiver member to exert a force on at least one of the inner ring, the outer ring, and the head portion of the shank.

18. The method of claim 13, further comprising passing the outer ring proximally through the aperture in a first orientation in which a longitudinal axis of the central opening of the outer ring is transverse to a longitudinal axis of the aperture and then rotating the outer ring to a second orientation in which the longitudinal axis of the central opening of the outer ring is coaxial with the longitudinal axis of the aperture and in which the outer ring cannot be passed distally through the aperture.

19. The method of claim 13, wherein the method is performed intraoperatively.

20. A method of assembling a bone anchor assembly, comprising:

advancing a head portion of a shank proximally through an aperture formed in a distal end of a receiver member;

proximally advancing the head portion of the shank into a central opening of an outer ring disposed within the receiver member such that an inner ring engaged between the head portion of the shank and the outer ring locks the position of the shank relative to the outer ring, prior to advancing the head portion of the shank into the central opening of the outer ring, coupling the inner ring to one of the head portion of the shank and the outer ring, wherein the inner ring is coupled to the head portion of the shank by expanding the inner ring and engaging an annular projection formed on one of the head portion of the shank and an inner surface of the inner ring with a complementary annular groove formed in the other one of the inner surface of the inner ring and the head portion of the shank; and polyaxially rotating a position of the outer ring relative to the receiver member.

21. A method of assembling a bone anchor assembly, comprising:

advancing a head portion of a shank proximally through an aperture formed in a distal end of a receiver member;

proximally advancing the head portion of the shank into a central opening of an outer ring disposed within the receiver member such that an inner ring engaged between the head portion of the shank and the outer ring locks the position of the shank relative to the outer ring;

passing the outer ring proximally through the aperture in a first orientation in which a longitudinal axis of the central opening of the outer ring is transverse to a longitudinal axis of the aperture and then rotating the outer ring to a second orientation in which the longitudinal axis of the central opening of the outer ring is coaxial with the longitudinal axis of the aperture and in which the outer ring cannot be passed distally through the aperture;

polyaxially rotating a position of the outer ring relative to the receiver member.

\* \* \* \* \*